Figure 1:
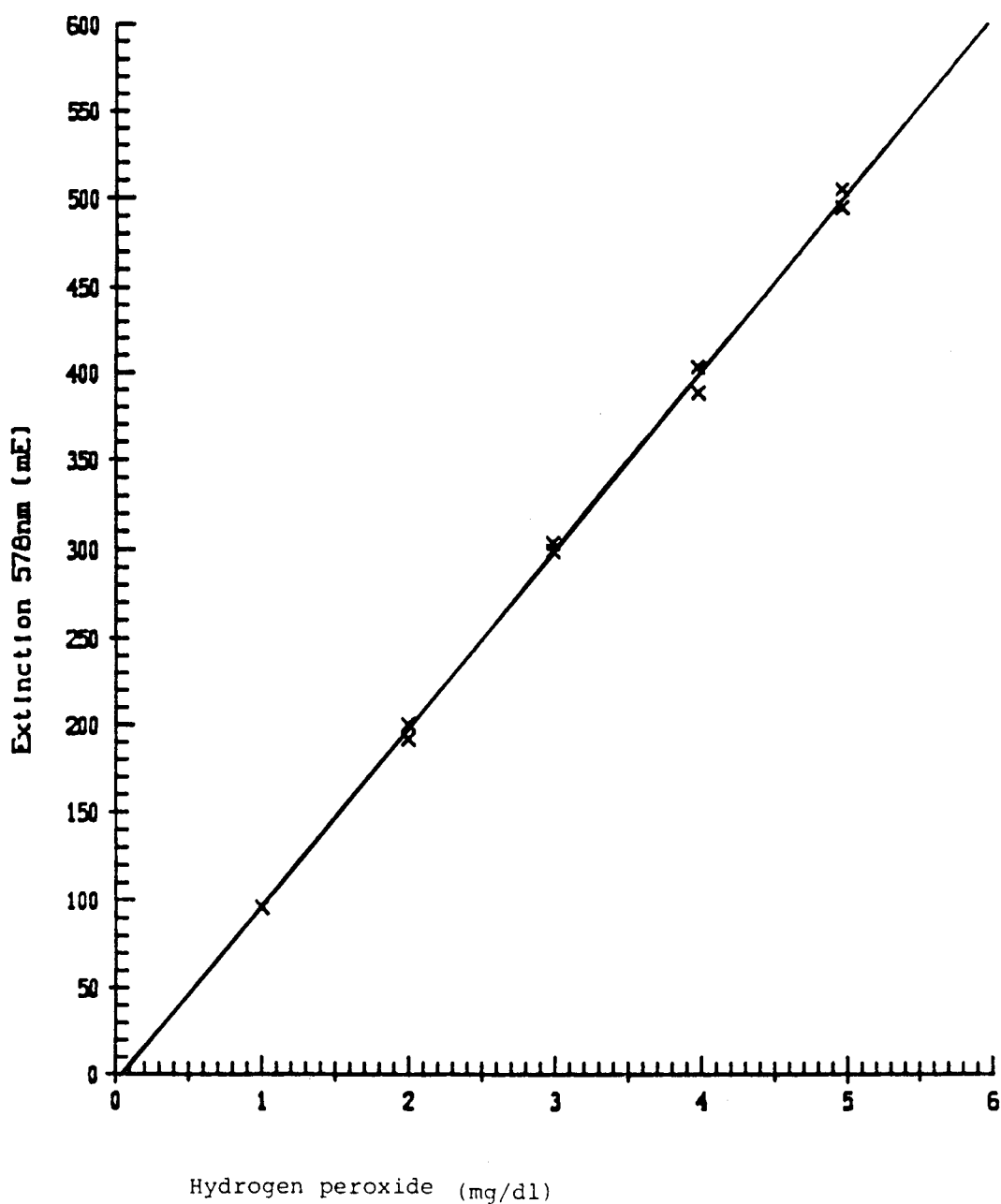

United States Patent [19]

Klein et al.

[11] Patent Number: 4,737,466
[45] Date of Patent: Apr. 12, 1988

[54] N-ACYLDIHYDRORESORUFIN DERIVATIVES, PROCESSES FOR THEIR PREPARATION, REAGENTS CONTAINING THEM AND THE USE THEREOF FOR DETERMINING HYDROGEN PEROXIDE, PEROXIDATE-ACTING COMPOUNDS OR PEROXIDASE

[75] Inventors: Christian Klein; Herbert Von Der Eltz; Rupert Herrmann, all of Weilheim; Martina Junius, Bernried, all of Fed. Rep. of Germany

[73] Assignee: Boehringer Mannheim GmbH, Mannheim, Fed. Rep. of Germany

[21] Appl. No.: 884,372

[22] Filed: Jul. 11, 1986

[30] Foreign Application Priority Data

Jul. 25, 1985 [DE] Fed. Rep. of Germany ....... 3526566

[51] Int. Cl.⁴ .................... G01N 33/52; G01N 33/72; C12Q 1/28
[52] U.S. Cl. ....................... 436/135; 436/66; 436/904; 435/28; 544/101
[58] Field of Search ............ 436/66, 135, 904; 435/28; 544/101

[56] References Cited

U.S. PATENT DOCUMENTS 4,556,640 12/1985 Ganter .......................... 436/904 X
4,567,139 1/1986 Batz .............................. 436/904 X

*Primary Examiner*—David L. Lacey
*Assistant Examiner*—Jill Johnston
*Attorney, Agent, or Firm*—Felfe & Lynch

[57] ABSTRACT

The present invention provides N-acylidihydroresorufin derivatives of the general formula:

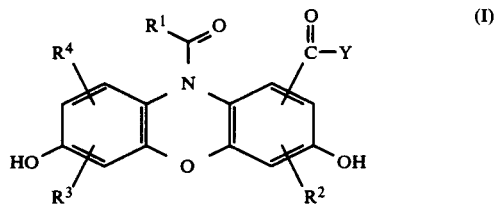

wherein $R^1$ is a lower alkyl, aryl or aralkyl radical, which can be substituted by carboxyl or sulphonic acid residues, $R^2$, $R^3$ and $R^4$, which can be the same or different, are hydrogen or halogen atoms or lower alkyl or lower alkoxy radicals, Y is an $-NR^5R^6$ or $-OR^7$ group, wherein $R^5$ and $R^6$ are, in each case, hydrogen atoms or lower alkyl radicals, which can be substituted by carboxyl or sulphonic acid residues, or together represent a hydrocarbon bridge optionally interrupted by hetero atoms and $R^7$ is a lower alkyl radical which can be substituted by a lower alkoxy or poly-lower alkoxy radical.

16 Claims, 3 Drawing Sheets

FIG. I.

N-ACYLDIHYDRORESORUFIN DERIVATIVES, PROCESSES FOR THEIR PREPARATION, REAGENTS CONTAINING THEM AND THE USE THEREOF FOR DETERMINING HYDROGEN PEROXIDE, PEROXIDATE-ACTING COMPOUNDS OR PEROXIDASE

The present invention is concerned with new N-acyldihydroresorufin derivatives i.e. derivatives of 10-acyl-3,7-dihydroxy-phenoxazine, a process for the preparation thereof and the use thereof for the determination of hydrogen peroxide, peroxidate-acting compounds and peroxidase.

The reaction of hyrogen peroxide or of peroxidate-acting substances with oxidation indicators catalysed by peroxidase plays a special role in analytical chemistry. It permits not only the detection of hydrogen peroxide and of peroxidate-acting compounds, as well as of peroxidase and of substances with peroxidase activity, for example haemoglobin, but also the determination of a series of materials which react with oxygen in the presence of appropriate oxidases with the formation of hydrogen peroxide or of peroxidate-acting compounds and, finally, also the determination of these oxidases themselves. As examples, there are given some compounds, the appropriate oxidases for which are given in brackets: glucose (glucose oxidase), galactose (galactose oxidase), D-amino acids (D-amino acid oxidase), cholesterol (cholesterol oxidase), xanthine (xanthine oxidase), uric acid (uricase), glycerol (glycerol oxidase), pyruvate (pyruvate oxidase) and sarcosine (sarcosine oxidase).

Such determinations are usually carried out in such a manner that hydrogen peroxide reacts stoichiometrically in the presence of peroxidase with a chromogen to give a coloured material. The absorption of the reaction mixture is measured photometrically and is a measure for the amount of the reacted hydrogen peroxide and thus of the compound to be determined.

The detection reactions are usually carried out in cuvettes or with the help of dry reagent carriers. In the latter case, quantification takes place, for example, with photometers via a transmission measurement, with remission photometers via remission measurement or with the help of comparative colours by visual comparison.

Furthermore, the detection of peroxidase is necessary in the case of immunological test processes, for example ELISA (enzyme linked immunosorbent assay) in which peroxidase is used as labelling enzyme. In the case of such immunological test processes, the peroxidase concentration is usually of the order of magnitude of $<10^{-5}M$.

From the literature, numerous compounds are known for the above-mentioned methods which can be used as indicators for the detection of hydrogen peroxide or of peroxidase. As examples, there are here mentioned benzidine and benzidine derivatives, dichlorophenolindophenol, aminocarbazoles and coloured materials which are formed as products of the oxidative coupling of 4-aminoantipyrine or related compounds with phenols, naphthols, aniline derivatives and other coupling components.

In spite of the number of known redox indicators for the detection of hydrogen peroxide, peroxidate-acting compounds or peroxidase, such compounds are still sought after which can be used widely, i.e. in the most varied enzymatic test systems, possess a high sensitivity within the pH range mostly used for the enzymatic tests of from about neutral to weakly alkaline and are well suited for the most varied processes, for example UV photometric, visual and fluorimetric measurements.

It is an object of the present invention to provide appropriate peroxidase substrates which fulfil the above requirements. This object is achieved by the new N-acyldihydroresorufin derivatives according to the present invention.

Thus, according to the present invention, there are provided compounds of the general formula:

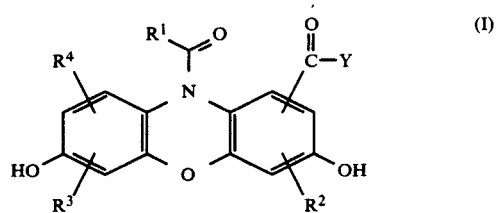

wherein $R^1$ is a lower alkyl, aryl or aralkyl radical, which can be substituted by carboxyl or sulphonic acid residues, $R^2$, $R^3$ and $R^4$, which can be the same or different, are hydrogen or halogen atoms or lower alkyl or lower alkoxy radicals, Y is an $-NR^5R^6$ or $-OR^7$ group, wherein $R^5$ and $R^6$ are, in each case, hydrogen atoms or lower alkyl radicals, which can be substituted by carboxyl or sulphonic acid residues, or together represent a hydrocarbon bridge optionally interrupted by hetero atoms and $R^7$ is a lower alkyl radical which can be substituted by a lower alkoxy or poly-lower alkoxy radical.

By lower alkyl and lower alkoxy radicals used in the definitions of the substituents $R^1$, $R^2$, $R^3$, $R^4$, $R^5$, $R^6$ and $R^7$ are to be understood saturated straight-chained and branched hydrocarbon radicals containing up to 7 and preferably up to 4 carbon atoms, the methyl, ethyl, methoxy and ethoxy radicals being especially preferred.

The poly-lower alkoxy radical in the definition of the substituents of $R^7$ consists of 2 to 5 and preferably of 2 to 3 lower alkoxy moieties.

As aryl radical in the definition of $R^1$ there is especially preferred a phenyl or naphthyl radical. The aralkyl radical in the definition of $R^1$ preferably contains, as aryl moiety, a phenyl or naphthyl radical and the alkyl moiety contains up to 5 and preferably up to 3 carbon atoms, a benzyl radical being especially preferred as an aralkyl radical.

The lower alkyl, aryl and also aralkyl radicals in the definitions of the substituents $R^1$, $R^5$ and $R^6$ can, in each case, be substituted one or more times by carboxy and sulphonic acid residues, radicals being preferred which contain up to 3 such substituents.

By halogen in the definitions of $R^2$, $R^3$ and $R^4$ are to be understood fluorine, chlorine, bromine and iodine, chlorine and bromine being preferred.

The hydrocarbon bridge optionally interrupted by heteroatoms, which can be formed by the substituents $R^5$ and $R^6$, preferably contains 2 to 5 and especially 3 or 4 carbon atoms. The hydrocarbon bridge can be interrupted by up to 3 heteroatoms selected from oxygen, nitrogen and sulphur. The morpholine and piperazine radicals are especially preferred.

The new compounds of general formula (I) can be prepared by known methods. According to a preferred process for the preparation of compounds of general formula (I), a compound of the general formula:

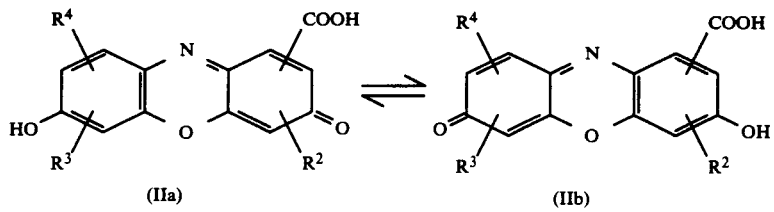

in which $R^2$, $R^3$ and $R^4$ have the meanings given in general formula (I), is reduced and acylated to give a compound of the general formula:

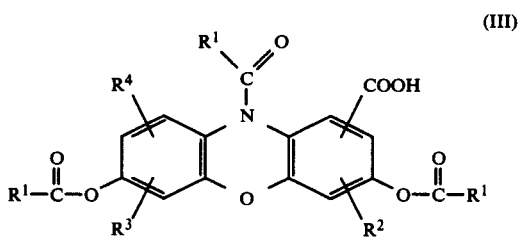

in which $R^1$, $R^2$, $R^3$ and $R^4$ have the meanings given in general formula (I), the latter, optionally after conversion of the carboxylic acid function into a reactive carboxylic acid derivative, is reacted with a compound of the general formula:

HY  (IV)

in which Y has the meaning given in general formula (I), and subsequently the O-acyl radicals are selectively split off.

The compounds of general formulae (IIa) and (IIb) are either known substances, which are derived from resorufin, or they can be prepared analogously to known processes.

For this purpose, a nitrosoresorcinol derivative of the general formula:

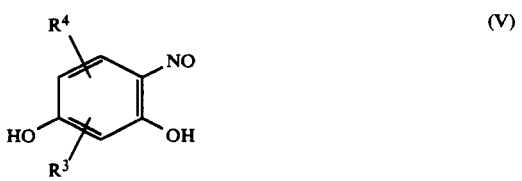

wherein $R^3$ and $R^4$ have the meanings given in general formula (I), is reacted with a resorcinol derivative of the general formula:

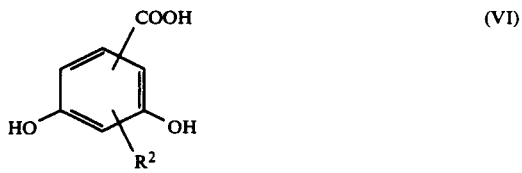

wherein $R^2$ has the meaning given in general formula (I), in the presence of pyrolusite and sulphuric acid at a low temperature. There is thereby first formed a resazurin derivative in which the nitrogen atom still carries an oxygen atom. This compound can easily be converted with zinc powder in the presence of ammonia into a compound of general formula (IIa) or (IIb).

The reaction of compounds of general formula (V) with compounds of general formula (VI) is usually carried out at a temperature of from −10° to 50° C. and preferably of from 0° to 30° C. The reaction takes place especially gently when the compounds of general formulae (V) and (VI) are mixed at about 0° C. and the reaction mixture is subsequently allowed to warm up to ambient temperature. The concentration of the pyrolusite should preferably be from 0.5 to 5 and especially of from 1 to 2 mole/liter. The sulphuric acid concentration should be from 0.5 to 5 and preferably from 1 to 3 mole/liter.

The reduction of the resazurin derivative initially formed to give a compound of general formula (IIa) or (IIb) is preferably carried out in ammoniacal solution with zinc dust (cf. Nietzki et al., Ber. Dtsch. Chem. Ges., 22, 3020/1889) or with sodium borohydride. As solvent, there is preferably used a water-alcohol mixture and preferably a mixture of 1 part of water with 0 to 4 parts of methanol. Per mole of compound to be reduced, there are used to 1 to 20 and preferably 1 to 5 mole of zinc dust or sodium borohydride, which is added portionwise. The temperature of the reaction solution is thereby kept at −10° to +35° C. and preferably at +5 to +10° C. The exact maintenance of the temperature range has proved to be necessary for the precise course of the reaction. Without cooling, the exothermal reaction gives rise to by-products which are difficult to separate.

Under the chosen mild conditions, the reaction between the compounds of general formula (V) and those of general formula (VI) takes place unambiguously and with good yield. The selected synthesis route is capable of variation. Especially having regard to the preparation of asymmetrically substituted resorufin derivatives, this opens up numerous possibilities of synthesis.

For the preparation of the triacyl derivatives of general formula (III), the appropriate resorufin derivatives of general formulae (IIa) and (IIb) are first reduced with a strong reducing agent, for example stannous chloride or chromic acetate, or electrochemically. For the reduction, the resorufin derivative is heated for from 10 to 60 minutes with 2 to 10 and preferably 2 to 6 equivalents of the reducing agent in an appropriate solvent and preferably with stannous chloride in 5 to 35% aqueous hydrochloric acid. Upon cooling, the dihydro compound precipitates out. The acylation takes place in the usual manner with an appropriate acylation agent, for example acetic anhydride, benzoyl chloride or the like. The compounds of general formula (III) are preferably prepared in a one-pot process by reductive acylation of the resorufin derivatives (IIa) and (IIb). The appropriate resorufin derivative is, for this purpose, heated under reflux with 2 to 6 equivalents of the reducing agent in the presence of the acylation agent in an appropriate solvent for 5 minutes to 3 hours or is stirred at ambient temperature for from 4 to 16 hours.

For the reaction of the compounds (IV), it is preferable to convert the carboxylic acid of general formula (III) into a reactive carboxylic acid derivative, for example a carboxylic acid chloride, ester or anhydride. For this purpose, numerous processes are known from the literature. In particular, it is preferred to convert the carboxylic acid function into a carboxylic acid chloride, for example with oxalyl chloride/dimethylformamide for thionyl chloride/dimethylformamide.

The compounds of general formula (IV) are amines or alcohols with which the carboxylic acid derivatives of general formula (III) or the reactive derivatives thereof are converted into carboxylic acid amides or esters, for example in the presence of an acylation catalyst, such as dimethylaminopyridine.

Especially preferred amines of general formula HY are those with a polar group, for example morpholine, methoxyethylamine or glycinamide, because the water-solubility of the corresponding leucoresorufin derivative is thereby increased. Aminocarboxylic acids can be used in the same way. It is preferable to protect functional groups, which do not participate in the reaction, in the usual manner. Examples of such protected aminocarboxylic acids include glycine tert.-butyl esters, glycine benzyl esters and N-BOC lysine methyl esters. The protective groups introduced are, after the reaction has taken place, again split off in known manner.

As alcohols of the general formula HY, in principle all possible alcohols can be used. It is especially preferred to use diethylene glycol monoethyl ether and triethylene glycol monoethyl ether, as well as the corresponding monomethyl ethers.

For the preparation of the N-acyl derivatives of general formula (I) according to the present invention, after the reaction of the carboxylic acids (III) with amines or alcohols (IV), the two O-acyl radicals must be split off selectively. This is achieved by reaction with 2 to 10 mole and preferably 2 to 4 mole of sodium sulphite in a mixture of water and a water-soluble solvent, for example 1,4-dioxan, methanol or ethanol and preferably water/1,4-dioxan (1:1 v/v). The reaction temperature is from 20° to 100° C. and preferably from 80° to 100° C. Under these reaction conditions, the N-acyldihydroresorufin derivatives of general formula (I) according to the present invention can be prepared in high yields.

The N-acyl-dihydroresorufin derivatives of general formula (I) can easily be oxidised by hydrogen peroxide in the presence of peroxides to give coloured and fluorescing resorufin derivatives.

Consequently, the present invention is also concerned with the use of compounds of general formula (I) for the detection of hydrogen peroxide (or of peroxidate-acting compounds) or of peroxidase (or of substances with peroxidase activity). By means of such detection reactions, it is, of course, also possible to determine such materials which react with oxygen in the presence of appropriate oxidases with the formation of hydrogen peroxide or of peroxidate-acting compounds, as well as of enzyme activities in systems producing hydrogen peroxide or peroxidate-acting compounds.

The resultant oxidation products of the N-acyl-dihydroresorufin derivatives can be used not only for UV-photometric and visual detection but especially for fluorimetric measurements. This is of importance because, in comparison with photometric methods, the sensitivity of fluorimetric determinations is often increased by a power of ten. In some cases, it is necessary to work with fluorogenic substrates, for example in the case of investigations of enzymatic activities in cells with automatic apparatus for cell differentiation (cytofluorometry), as well as in the case of the analysis of immobilised enzymes with flowthrough microfluorometry. In other cases, for example in the case of the determination of enzymatic labellings of test systems (enzyme immunoassays), which are often carried out with peroxidase, the multiplication effect of the enzymatic catalysis is considerably strengthened by the use of fluorogenic substrates.

Not only the light absorption in the UV and visible range but also the intensity of the fluorescence of the oxidation products of the compounds of general formula (I) according to the present invention are practically pH-independent in the neutral to weakly alkaline pH range. Since the pH value of the solution must be optimised, depending upon the enzyme system investigated, in order to achieve maximum activity and thus can be varied within a pH range of from 6.5 to 9.5, the pH-independence of the light absorption and of the intensity of fluorescence is also very important for the achievement of a comparably high sensitivity in different enzymatic tests.

In this connection is to be especially emphasised the good water-solubility of the N-acyl-dihydroresorufin derivatives according to the present invention in the mentioned pH range. Consequently, it is not necessary to add organic solvents or detergents to the enzymatic tests in order to bring the chromogen used into solution. This advantage manifests itself, inter alia, in the case of kinetic enzyme tests where good solubilities of substrate and product are necessary and where the addition of solvents or detergents often influence the enzyme activities.

For the determination of hydrogen peroxide or of peroxidate-acting compounds, a compound of general formula (I), peroxidase, an appropriate buffer system, as well as possibly further reagents and adjuvants, are mixed with the sample which contains the material to be determined, the N-acyl-dihydroresorufin derivatives of general formula (I) thereby being oxidised. The change of the absorption or of the intensity of fluorescence thereby brought about is measured photometrically or fluorimetrically. By direct comparison with a standard solution or by indirect comparison with a standard curve, there can thus be determined the content of the substance to be determined in the sample. Not only kinetic but also end point measurements are possible.

For the determination of peroxidase or of compounds with peroxidase activity, a compound of general formula (I), hydrogen peroxide or a peroxidate-acting compound, an appropriate buffer system, as well as possibly further reagents and adjuvants, are mixed with the sample which contains the material to be determined. The reaction mixture obtained is further treated in the above-described manner.

The compounds of general formula (I) can also be used for the determination of substances which, with oxygen in the presence of appropriate oxidases, give hydrogen peroxide or peroxidate-acting compounds, or of enzyme activities in systems producing hydrogen peroxide or peroxidate-acting compounds. The determination of these substances or of these enzymes takes place in the above-described manner except that the appropriate oxidases, as well as possibly further adjuvent enzymes or the appropriate substrate, are additionally added to the reaction mixture. As examples of such enzymatic systems, there may be mentioned the reactions of glucose to give gluconolactone with glucose oxidase, of cholesterol to give cholestenone with cholesterol oxidase, of uric acid to allantoin with uricase or of glycerol or glyceraldehyde with glycerol oxidase. The concentrations of such substrates or enzymes in body fluids are important diagnostic parameters which, in the same manner, can be determined simply and exactly.

Thus, the present invention also provides a process for the determination of hydrogen peroxide, of peroxidate-acting compounds and of substances which, with oxygen in the presence of appropriate oxidases, give rise to hydrogen peroxide or of peroxidate-acting compounds, as well as a process for the determination of peroxidase, of compounds with peroxidase activity and of enzyme activities in systems producing hydrogen peroxide or peroxidate-acting compounds with the use of compounds of general formula (I).

The present invention also provides reagents which can be used for carrying out the above-mentioned process. A reagent for the detection of hydrogen peroxide, of peroxidate-acting compounds and of substances which give rise to such compounds contains, besides one or more of the N-acyl-dihydroresorufin derivatives of general formula (I) according to the present invention, peroxidase, as well as further enzymes necessary for the particular parameter detection, an appropriate buffer system, as well as optionally further reagents and adjuvants, for example wetting agents, stabilizers, galenical additives, structure formers and the like.

The reagent for the detection of peroxidase, of compounds with peroxidase activity and of enzyme activities of systems producing hydrogen peroxide or peroxidate-acting compounds contains, besides one or more of the N-acyl-dihydroresorufin derivatives of general formula (I), hydrogen peroxide or a peroxidate-acting compound, optionally necessary substrates and adjuvant enzymes, an appropriate buffer system, as well as possibly further reagents and adjuvants.

The reagent according to the present invention can be in the form of a solution, a lyophilisate, a powder mixture or a reagent tablet or can be applied to an approprite carrier material.

The reagent according to the present invention in the form of a solution preferably contains all of the reagents necessary for the test. As solvent, there can be used water or a mixture of water with a water-soluble organic solvent, for example methanol, ethanol, acetone or dimethylformamide. For reasons of storage stability, it can be advantageous to divide the reagents needed for the test into two or more solutions which are only mixed upon carrying out the actual investigation.

For the preparation of the reagent in the form of a lyophilisate, a solution is dried which contains, besides the reagents required for the test, conventional structure formers, for example polyvinylpyrrolidone and possibly further filling materials, for example mannitol, sorbitol or xylitol.

A reagent in the form of a powder mixture or of a reagent tablet can be prepared by mixing the components of the test with conventional galenical additives, followed by granulation. Additional materials of this kind include, for example, sugar alcohols, such as mannitol, soritol and xylitol, or other soluble inert compounds, such as polyethylene glycols and polyvinylpyrrolidone. In general, the powder mixtures or reagent tablets have an end weight of about 30 to 200 mg. and preferably of from 50 to 80 mg.

As carrier materials for test strips, there can be used known carrier materials, for example paper, glass or synthetic resin fleece, meshes or fabrics of fibrous materials or absorbent, porous films or gels.

For the production of the reagent in the form of a test strip, an appropriate carrier material, preferably filter paper, cellulose or synthetic resin fleece, is impregnated with solutions of the necessary reagents usually employed for the production of test strips in readily volatile solvents, for example water, methanol, ethanol or acetone. This can take place in a single impregnation step. However, it is often advisable to carry out the impregnation in several steps, solutions being used which, in each case, contain a part of the components of the reagent. Thus, for example, in a first step, impregnation can be carried out with an aqueous solution which contains the buffer and other water-soluble additives and then, in a second step, with a solution which contains the N-acyl-dihydrosorufin derivative. The finished test paper can be used as such or can be stuck in known manner on to a handle or preferably sealed between synthetic resin and a fine mesh in the manner described in Federal Republic of Germany Patent Specification No. 2118455.

For the production of dry reagents from soluble film formers, solutions are prepared from the polymers which are so viscous that films can be produced therefrom according to known production processes, for example raking, forehand process, roll coating or the like. The reagents, buffer substances, adjuvants and reagent stabilisers are incorporated into these solutions and the coating masses are applied to carrier films and dried, the finished films being worked up to give test strips.

N-acyl-dihydroresorufin derivatives of general formula (I) can also be used for immunological methods of determination in which peroxidase is used as the indicator enzyme and the activity of which must be determined after carrying out the immunological reaction. Such immunological methods of determination with an enzymatic indicator reaction are known as enzyme immunoassays. These methods are used for the determination of the concentrations of proteins, polysaccharides, hormones, pharmaceuticals and other low-molecular weight substances in the range of from $10^{-5}$ to $10^{-12}$ mole/liter. Depending upon the requirement of phase separation steps, a distinction is made between a homogeneous and a heterogeneous carrying out of the test. A further subdivision can be made between competitive and non-competitive test principles. However, all test principles work with enzyme-antigen or enzyme-antibody conjugates. The enzymatic indicator reaction is common to all enzyme immunoassays. An indicator enzyme appropriate for such purposes is, for example, peroxidase. The determination of peroxidase in such enzyme immunoassays usually takes place by adding an appropriate substrate which is enzymatically oxidised with hydrogen peroxide and is measured in the usual manner photometrically or also fluorimetrically.

The following Examples describe some of the process variants which can be used for the synthesis of the compounds according to the present invention, as well as, by way of example, the use of the new N-acyl-dihydroresorufin derivatives of general formula (I).

EXAMPLE 1

N-Acetyl-dihydroresorufin-4-carboxylic acid morpholide (A) Resorufin-4-carboxylic acid.

16 g. Nitrosoresorcinol, 15.5 g. 2,6-dihydroxybenzoic acid and 8.6 g. pyrolusite are suspended in 200 ml. methanol and cooled to 0° C. 10.6 ml. concentrated sulphuric acid are added dropwise thereto and the reaction mixture is then stirred for 2 hours at ambient temperature. The precipitated red resazurin-4-carboxylic acid is filtered off, washed with methanol and dried.

The resazurin derivative is taken up in 200 ml. water and 50 ml. 25% ammonia and filtered. To the blue filtrate is added portionwise, with ice cooling, 50 g. zinc dust and the reaction mixture is allowed to warm up to ambient temperature. The course of the reduction can easily be monitored by thin layer chromatography (elution agent: methanol/ethyl acetate 1:1 v/v; silica gel TLC plates). The reaction solution is filtered and the filtrate is thereafter acidified with glacial acetic acid and a little concentrated hydrochloric acid. The precipitated resorufin-4-carboxylic acid is filtered off and dried in a vacuum over Sicapent. Yield 16.33 g.; Rf (TLC: silica gel; elution agent: n-butanol/glacial acetic acid/water 4:1:1 v/v/v): 0.4.

(B) N,O,O-Triacetyl-dihydroresorufin-4-carboxylic acid. 12.9 g. Resorufin-4-carboxylic acid are taken up in 30 ml. glacial acetic acid and 30 ml. acetic ahydride, mixed with 27.6 g. stannous chloride and stirred for 1 hour at 80° C. 600 ml. ice water are added thereto, stirring is continued for 1 hour and the precipitate is then filtered off. After drying, the solid material is taken up in 500 ml. acetone, filtered with suction and the filtrate dried to give 11.3 g. of N,O,O-triacetyldihydroresorufin-4-carboxylic acid; Rf (TLC: silica gel; elution agent: chloroform/methanol/glacial acetic acid 9:1;0.1 v/v/v): 0.46.

$^1$H-NMR (D$_6$-DMSO): $\delta = 2.24$, 2.26 and 2.29 (each s, each 3H); 6.94 (dd, J=8.5 and 2.2 Hz, 1H); 6.98 (d, J=2.2 Hz, 1H); 7.94 (d, J=9 Hz, 1H); 7.61 (d, J=8.5 Hz, 1H); 7.67 ppm (d, J=9 Hz, 1H).

(c) N,O,O-Triacetyldihydroresorufin-4-carboxylic acid morpholide.

3.85 g. N,O,O-Triacetyldihydroresorufin-4-carboxylic acid are mixed with 5.4 ml, oxalyl chloride and cooled to 0° C. A drop of dimethylformamide is added thereto and the reaction is allowed to warm to ambient temperature, while stirring, the educt thereby dissolving with the evolution of gas. The reaction mixture is evaporated to dryness at ambient temperature in a vacuum, take up three times with 20 ml. amounts of methylene chloride and again evaporated to dryness. There are thus obtained 4 g. N,O,O-triacetyldihydroresorufin-4-carboxylic acid chloride which, as crude product, is further worked up.

The acid chloride is dissolved in 50 ml. dry methylene chloride and 3.1 ml. triethylamine are added dropwise thereto and subsequently 1.2 ml. morpholine. After stirring for 2 hours, the reaction solution is washed with water, saturated aqueous sodium hydrogen carbonate solution and dilute hydrochloric acid and the methylene chloride phase is dried over anhydrous magnesium sulphate and evaporated. The residue is crystallised from ethanol. There are obtained 8.1 g. N,O,O-triacetyldihydroresorufin-4-carboxylic acid morpholide.

$^1$H-NMR (D$_6$-DMSO): $\delta = 2.20$–2.21 (3 s, 9H); 3.50–3.80 (m, 8H); 6.70–7.05 (m, 2H); 7.12 (d, J=2 Hz, 1H); 7.54 (d, J=9 Hz, 1H); 7.60 ppm (d, J=9 Hz, 1H).

(D) N-Acetyldihydroresorufin-4-carboxylic acid morpholide.

2.02 g. N,O,O-triacetyldihydroresorufin-4-carboxylic acid morpholide are heated under reflux for 30 minutes with 1.2 g. anhydrous sodium sulphite in 50 ml. dioxan/water (1:1 v/v). The reaction mixture is evaporated and the residue is taken up in 50 ml. acetone, filtered and the filtrate again evaporated. The residue is chromatographed on silica gel (elution agent chloroform/methanol 8:2 v.v) and 1.0 g. N-acetyldihydroresorufin-4-carboxylic acid morpholide is obtained: Rf (TLC: silica gel; elution agent: chloroform/methanol 8.2 v/v): 0.8.
$^1$H-NMR (D$_6$-DMSO): $\delta$=2.20 (s, 3H); 3.10–3.16 (m, 2H); 3.4–3.8 (m, 6H); 6.48 (d, J=2.4 Hz, 1); 6.53 (dd, J=9.8 and 2.4 Hz, 1H); 6.62 (d, J=9 Hz, 1H); 7.30 (d, J=9.8 Hz, 1H); 7.33 (d, J=9.8 Hz, 1H); 9.62 (s, 1H); 9.91 ppm (s, 1H).

| | |
|---|---|
| UV/VIS (0.1 M potassium phosphate buffer, pH 7.5) | $\lambda_{max}$ = 200 nm |
| after oxidation with hydrogen peroxide/peroxidase | $\lambda_{max}$ = 575 nm |
| fluorescence emission | $\lambda_{max}$ = 590 nm |

In an analogous manner, there are obtained the following compounds;

(a) N-acetyl-6-methyldihydroresorufin-4-carboxylic acid morpholide
from 2-methyl-4-nitrosoresorcinol via 6-methylresazurin-4-carboxylic acid and 6-methylresorufin-4-carboxylic acid.
$^1$H-NMR (D$_6$-DMSO): $\delta$=2.17 and 2.23 (each 3, 6H); 3.5–3.8 m, 8H); 6.20 (d, J=8.6 Hz, 1H); 6.66 (d, J=8.8 Hz, 1H); 6.79 (d, J=8.8 Hz, 1H); 7.35 ppm (d, J=8.8 Hz, 1H).

| | |
|---|---|
| UV/VIS (0.1 M potassium phosphate buffer, pH 8.0) after oxidation with hydrogen peroxide/peroxidase | $\lambda_{max}$ = 585 nm |

(b) N-acetyl-8-ethyldihydroresorufin-4-carboxylic acid morpholide
from 4-ethyl-6-nitrosoresorcinol via 8-ethylresazurin-4-carboxylic acid and 8-ethylresorufin-4-carboxylic acid. TLC (silica gel, elution agent: ethyl acetate): Rf=0.38

| | |
|---|---|
| UV/VIS (0.1 M potassium phosphate buffer pH 8.0) | |
| after oxidation with hydrogen peroxide/peroxidase | $\lambda_{max}$ = 575 nm |
| fluorescence emission | $\lambda_{max}$ = 598 nm |

(c) N-acetyl-8-chlororesorufin-1-carboxylic acid morpholide
from 4-chloro-6-nitrosoresorcinol via 8-chlororesazurin-1-carboxylic acid and 8-chlororesorufin-1-carboxylic acid.

| | |
|---|---|
| UV/VIS (0.1 M potassium phosphate buffer, pH 8.0) after oxidation with hydrogen peroxide/peroxidase | $\lambda_{max}$ = 570 nm |

(d) N-acetyl-6,8-dichlorodihydroresorufin-4-carboxylic acid morpholide
from 2,4-dichloro-6-nitrosoresorcinol via 6.8-dichlororesazurin-4-carboxylic acid and 6,8-dichlororesorufin-4-carboxylic acid (e) N-acetyl-8-bromodihydroresorufin-4-carboxylic acid morpholide
from 4-bromo-6-nitrosoresorcinol via 8-bromoresazurin-4-carboxylic acid and 8-bromoresorufin-4-carboxylic acid.

EXAMPLE 2

N-Acetyldihydroresorufin-4-carboxylic acid carboxymethylamide (A) N,O,O-Turacetyldihyroresorufin-4-carboxylic acid tert.-butoxycarbonylmethylamide.

10.7 g. N,O,O-triacetyldihydroresorufin-4-carboxylic acid (prepared according to Example 1(b)) are, as described in Example 1(c)), converted into the acid chloride with 27 ml. oxalyl chloride and the acid chloride is taken up in 100 ml. methylene chloride. To this are added dropwise 7.8 g. glycine tert.-butyl ester dissolved in 20 ml. methylene chloride and the reaction mixture is stirred for 3 hours at ambient temperature. It is then washed with a saturated aqueous solution of sodium hydrogen carbonate, 1N citric acid and water. After drying over anhydrous magnesium sulphate, the organic phase is evaporated and the residue is taken up in a little ethyl acetate and filtered over silica gel with ethyl acetate as elution agent. There are obtained 11 g. N,O,O-triacetyldihydroresorufin-4-carboxylic acid tert.-butoxycarbonylmethylamide in the form of a light brownish coloured product; Rf (TLC: silica gel, elution agent: ethyl acetate): 0.68.

(B) N-Acetyldihydroresorufin-4-carboxylic acid tert.-butoxycarbonylmethylamide.

9 g. N,O,O-triacetyldihydroresorufin-4-carboxylic acid tert.-butoxycarbonylmethylamide are heated under reflux for 30 minutes with 4.6 g. anhydrous sodium sulphite in 100 ml. dioxan/water (1:1 v/v). The reaction mixture is evaporated and the residue is taken up in 250 ml. acetone, filtered and the fitlrate again evaporated. By crystallisation from ethanol, there are obtained 4.5 g of product. 1.4 g. thereof is chromatographed on silica gel with methylene chloride/methanol (20:1 v/v). Yield 0.9 g. N-acetyldihydroresorufin-4-carboxylic acid tert.-butoxycarbonylmethylamide. Rf (TLC: silica gel, elution agent: ethyl acetate): 0.77.

$^1$H-NMR (D$_6$-DMSO): $\delta$=1.49 (s, 9H); 2.20 (s, 3H); 4.07 (d, J=6 Hz, 2H); 6.61 (dd, J=9.8 and 2.4 Hz, 1H); 6.69 (d, J=9.8 Hz, 1H); 6.86 (d, J=2.4 Hz, 1H); 7.35 (d, J=9.8 Hz, 1H); 7.51 (d, J=9.8 Hz, 1H); 8.77 (t, broad, J=6 Hz, 1H); 9.74 (s, 1H); 12.61 (s, 1H).

(C) N-Acetyldihydroresorufin-4-carboxylic acid carboxymethylamide.

500 mg. N-acetyldihydroresorufin-4-carboxylic acid tert.-butoxycarbonylmethylamide are left to stand for 30 minutes in 10 ml. trifluoroacetic acid. 40 ml. water are slowly added dropwise thereto, filtered, washed with water and dried. There are obtained 410 mg. N-acetyldihydroresorufin-4-carboxylic acid carboxymethylamide. Rf (TLC: silica gel; elution agent: n-butanol/glacial acetic acid/water 4:1:1 v/v/v): 0.79.
$^1$H-NMR: (D$_6$-DMSO): $\delta$=2.20 (s, 3H); 4.08 (d, J=6 Hz, 1H); 6.61 (dd, J=9.8 and 2.4 Hz, 1H); 6.69 (d, J=9.8 Hz, 1H); 6.89 (d, J=2.4 Hz, 1H); 7.34 and 7.52 (each d, J=9.8 Hz, 2H); 8.81 (t, broad, J=7 Hz, 1H); 9.74 (s, broad, 1H); 12.5 ppm (s, 1H).

| | |
|---|---|
| UV/VIS (0.1 M potassium phosphate buffer, pH 7.5) | $\lambda_{max} = 204$ nm |
| after oxidation with hydrogen peroxide/peroxidase | $\lambda_{max} = 571$ nm |
| fluorescence emission | $\lambda_{max} = 588$ nm |

In an analogous manner, there are obtained:

(a) from N,O,O-triacetyldihydroresorufin-4-carboxylic acid and sarcosine tert.-butyl ester via N,O,O-triacetyldihydroresorufin-4-carboxylic acid (tert.-butoxycarbonylmethyl)-methylamide (Rf TLC: silica gel; elution agent: chloroform/methanol/glacial acetic acid 9:1:0.1 v/v/v; 0.77) and N-acetyl-dihydroresorufin-4-carboxylic acid (tert.-butoxycarbonylmethyl)-methylamide (RF TLC as above: 0.56):

N-acetyldihydroresorufin-4-carboxylic acid (carboxymethyl)-methylamide; Rf (TLC as above): 0.10

| | |
|---|---|
| UV/VIS (0.1 M potassium phosphate buffer, pH 7.5) | $\lambda_{max} = 204$ nm |
| after oxidation with hydrogen peroxide/peroxidase | $\lambda_{max} = 574$ nm |

(b) N-acetyl-6-methyldihydroresorufin-4-carboxylic acid (carboxymethyl)-methylamide: Rf (TLC as above): 0.62

| | |
|---|---|
| UV/VIS (0.1 M potassium phosphate buffer, pH 7.5) | $\lambda_{max} = 205$ nm |
| after oxidation with hydrogen peroxide/peroxidase | $\lambda_{max} = 585$ nm |

(c) N-acetyl-8-chlordihydroresorufin-4-carboxylic acid carboxymethylamide

EXAMPLE 3

Determination of hydrogen peroxide.

To a solution of

| | |
|---|---|
| tris-(hydroxymethyl)-methyl-2-aminoethanesulphonate (pH 8) | 0.1 mmol/liter |
| Triton × 100 | 0.5% |
| N—acetyldihydroresorufin-4-carboxylic acid morpholide | 2.5 mmol/liter |
| peroxidase | 3 U/ml. | are pipetted differing amounts of a solution of known hydrogen peroxide content, left to stand for 60 minutes and thereafter the extinction measured at 578 nm.

In FIG. 1 of the accompanying drawings, the extinction at 578 nm is plotted against the hydrogen peroxide concentration in the measurement solution. A good linearity is obtained between the hydrogen peroxide concentration and the extinction.

With the help of a calibration curve obtained in this manner, there can also be determined the hydrogen peroxide concentration in samples of unknown hydrogen peroxide content.

EXAMPLE 4

Determination of creatinine

Solution 1:

| | |
|---|---|
| tris-(hydroxymethyl)-methyl-2-aminoethylsulphonate (pH 8) | 100 mmol/liter |
| Triton × 100 | 0.5% |
| N—acetyldihydroresorufin-4-carboxylic acid morpholide | 2.5 mmol/liter |
| sodium chloride | 150 mmol/l. |
| sodium cholate | 5 mmol/l. |
| EDTA | 0.5 mmol/l. |
| potassium ferrocyanide | 10 µmol/l. |
| sodium azide | 0.2% |
| peroxidase | 3 U/ml. |
| lipase | 2 U/ml. |
| ascorbate oxidase | 10 U/ml. |
| creatinase | 6.5 U/ml. |
| sarcosine oxidase | 6.5 U/ml. |
| creatininase | 25 U/ml. |

Solution 2:

| | |
|---|---|
| creatinine standard solution | 2 mg./100 ml. |

Figure 2:
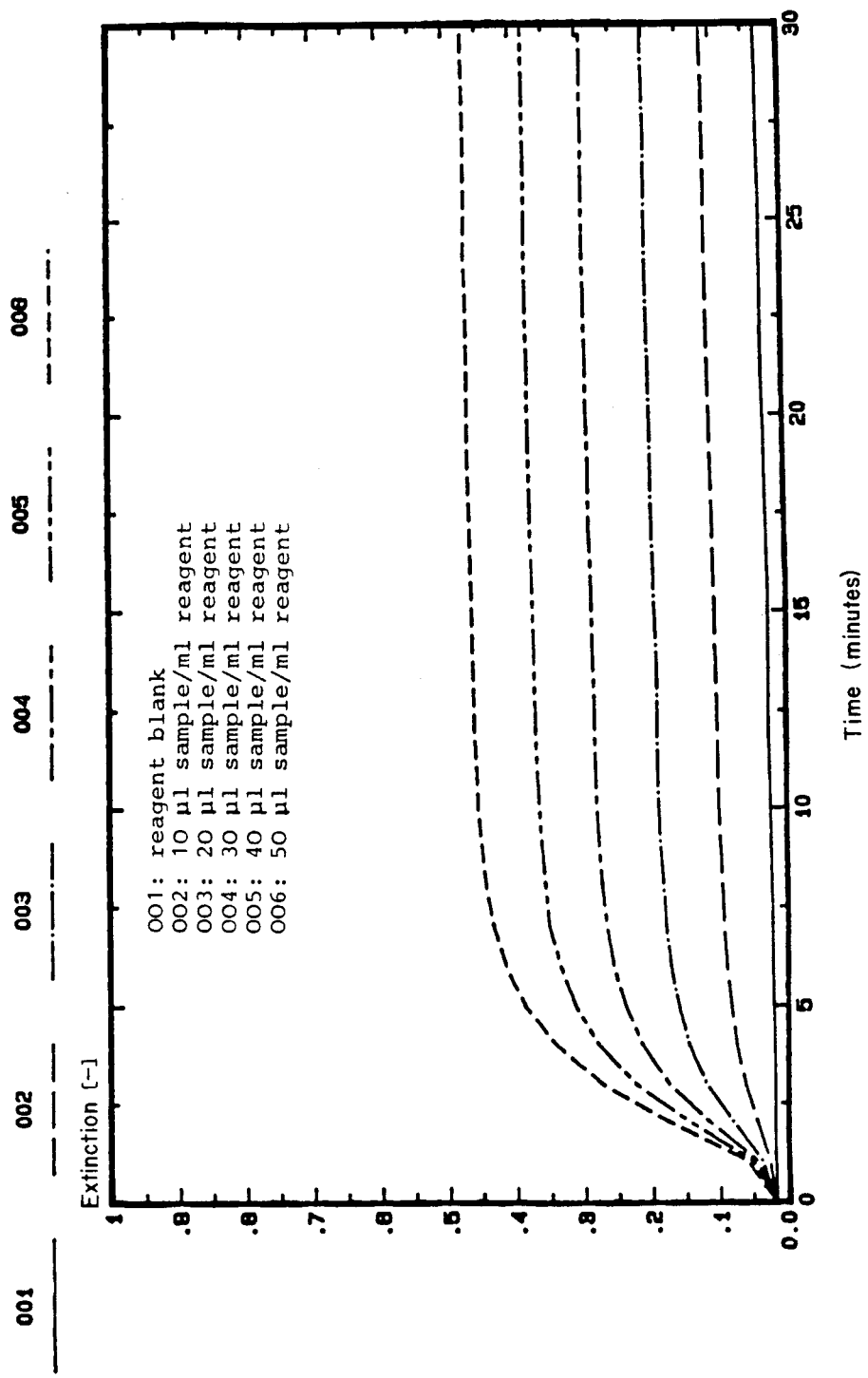

10, 20, 30, 40 and 50 µl. of Solution 2 are introduced into 1 ml. of Solution 1. The extinction is monitored in dependence upon the time. There is thus obtained the curve course shown in FIG. 2 of the accompanying drawings, which can be used as calibration curve for the determination of unknown creatinine concentrations.

EXAMPLE 5

Determination of thyroxin

Solution 1:

| | |
|---|---|
| potassium barbiturate | 120 mmol/liter |
| potassium phosphate buffer (pH 8.6) | 18.2 mmol/l. |
| 8-anilino-1-naphthalenesulphonic acid | 1.2 mmol/l. |
| bovine serum albumin | 0.2% |
| thyroxin-peroxidase conjugate | 0.5 U/l. |

Solution 2:

| | |
|---|---|
| tris/HCl (pH 8.0) | 100 mmol/l. |
| sodium perborate | 3.2 mmol/l. |
| N—acetyldihydroresorufin-4-carboxylic acid morpholide | 1.82 mmol/l. |

Figure 3:
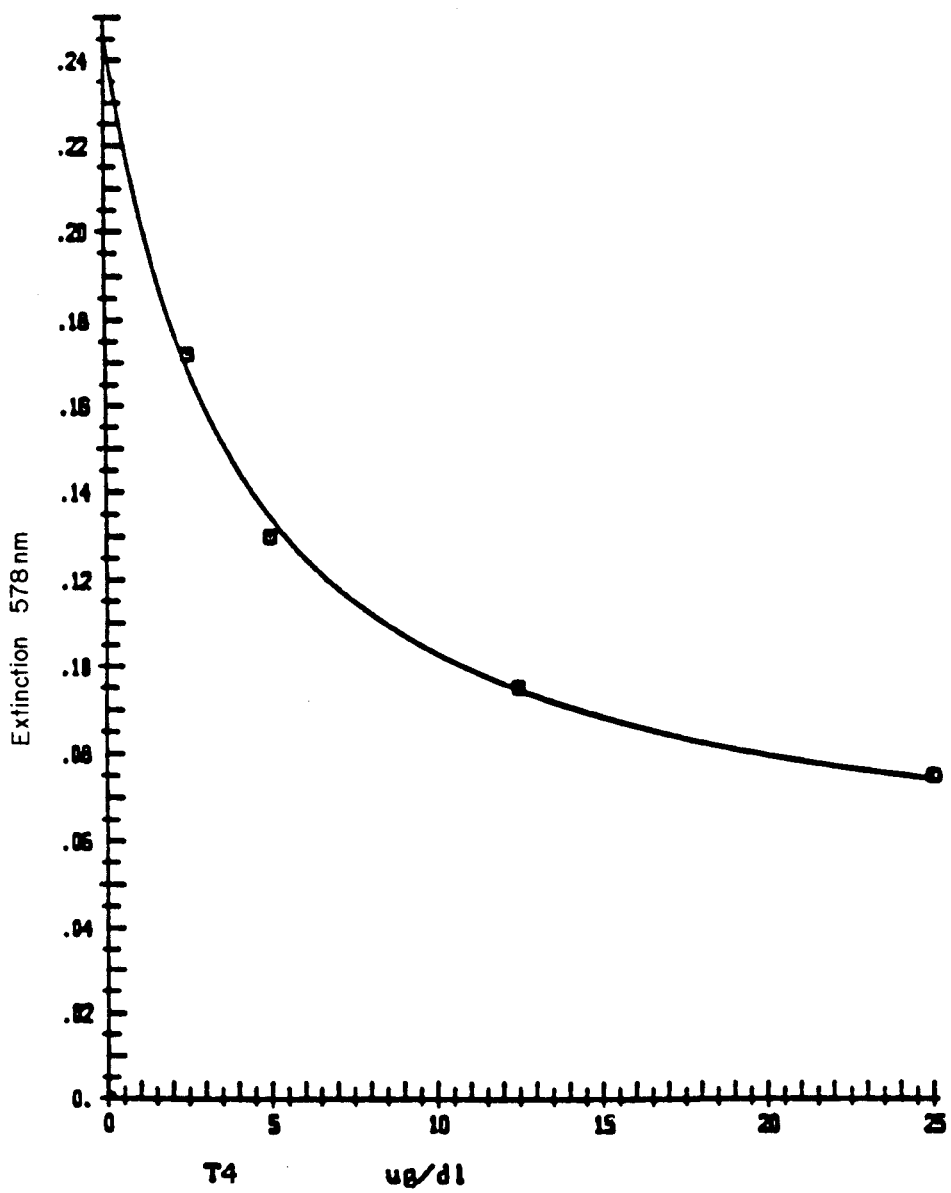

Into a synthetic resin test tube coated with anti-thyroxin antibody (binding capacity about 25 ng. thyroxin per test tube) are introduced 0.02 ml. thyroxin solution and 1 ml. Solution 1 and left to incubate for 30 minutes at 20° to 25° C. The content of the test tube is sucked off and the test tube is rinsed once with water and again sucked off. Thereafter, incubation is carried out for 60 minutes with Solution 2, thoroughly mixed and the extinction measured at 578 nm. The calibration curve thus obtained is illustrated in FIG. 3 of the accompanying drawings.

On the basis of such a calibration curve, there can be determined the unknown thyroxin content of a sample.

It will be understood that the specification and examples are illustrative but not limitative of the present invention and that other embodiments within the spirit and scope of the invention will suggest themselves to those skilled in the art.

What is claimed is:

1. An N-acyldihydroresorufin derivative of the formula:

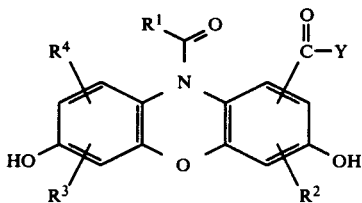

wherein

R$^1$ is a C$_1$-C$_7$ alkyl, C$_6$-C$_{10}$ aryl or aralkyl wherein said aralkyl has 6 to 10 carbon atoms in the aryl moiety and 1-5 carbon atoms in the alkyl moiety and wherein said alkyl or said aryl as well as said aryl or alkyl moiety in the aralkyl are unsubstituted or substituted by carboxyl or sulphonic acid residues, R$^2$, R$^3$ and R$^4$, which can be the same or different, are hydrogen, halogen, C$_1$-C$_7$ alkyl or C$_1$-C$_7$ alkoxy, Y is —NR$^5$R$^6$ or —OR$^7$ wherein R$^5$ is hydrogen or a C$_1$-C$_7$ alkyl, wherein said alkyl is unsubstituted or substituted by one or more carboxyl or sulphonic acid residues, and R$^6$ is hydrogen or a C$_1$-C$_7$ alkyl wherein said alkyl is unsubstituted or substituted by one or more carboxyl or sulphonic acid residues or R$^5$ and R$^6$ together represent a C$_2$-C$_5$ hydrocarbon bridge interrupted by 0 to 3 hetero atoms selected from the group consisting of oxygen, nitrogen and sulphur, and R$^7$ is C$_1$-C$_7$ alkyl, or C$_1$-C$_7$ alkyl substituted by a C$_1$-C$_7$ alkoxy or poly-C$_1$-C$_7$ alkoxy consisting of 2-5 alkoxy groups comprising 1 to 7 carbon atoms.

2. The derivative of claim 1 wherein R$_1$ is selected from the group consisting of phenyl, naphthyl, phenyl carrying a C$_1$-C$_5$ alkyl moiety and naphthyl carrying a C$_1$-C$_5$ alkyl moiety.

3. The derivative of claim 1 wherein R$_1$ is benzyl.

4. The derivative of claim 1 wherein said N-acyldihydroresorufin derivative is selected from the group consisting of N-acetyldihydroresorufin-4-carboxylic acid morpholide, N-acetyl-8-bromodihydroresorufin-4-carboxylic acid morpholide, N-acetyldihydroresorufin-4-carboxylic acid carboxymethylamide and N-acetyl-8-chlorodihydroresorufin-4-carboxylic acid carboxymethylamide.

5. The derivative of claim 1 wherein one or more of the substituents R$^1$, R$^2$, R$^3$, R$^4$, R$^5$, R$^6$ and R$^7$ are C$_1$-C$_7$ alkyl or alkoxy.

6. The derivative of claim 5 wherein alkyl is methyl or ethyl and alkoxy is methoxy or ethoxy.

7. The derivative of claim 1 wherein Y is —NR$^5$R$^6$ and R$^5$ and R$^6$ together represent a C$_2$-C$_5$ hydrocarbon bridge interrupted by up to 3 heteroatoms selected from the group consisting of oxygen, nitrogen and sulphur.

8. The derivative of claim 7 wherein the —NR$^5$R$^6$ moiety represents the morpholine radical.

9. A process for the determination of hydrogen peroxide, peroxidate-acting compounds or substances which produce hydrogen peroxide or peroxidate-acting compounds with oxygen in the presence of appropriate oxidases, comprising mixing one or more of an N-acyldihydroresorufin derivative according to claim 1, peroxidase and a buffer, with a sample containing a substance to be determined and measuring the change in absorption or emitted fluorescence as a measure of the substance to be determined.

10. A process for the determination of peroxidase, of compounds with peroxidase activity or of enzyme activities in systems producing hydrogen peroxide or peroxidate-acting compounds, comprising mixing one or more of an N-acyldihydroresorufin derivative according to claim 1, hydrogen peroxide or a peroxidate-acting compound, and a buffer with the sample which contains a substance to be determined and measuring the change in absorption or emitted fluorescence as a measure of the substance to be determined.

11. In a reagent for the detection of hydrogen peroxide, peroxidate-acting substances or substances which provide hydrogen peroxide or peroxidate-acting compounds with oxygen in the presence of appropriate oxidases, and wherein said reagent contains peroxidase as well as further necessary enzymes, one or more chromogenic or fluorogenic substrates and an appropriate buffer, the improvement wherein an N-acyldihydroresorufin derivative according to claim 1 is used as a chromogenic or fluorogenic substrate.

12. The reagent of claim 11 further comprising one or more wetting agents, stabilizers, galenical additives, organic acids structure formers.

13. The reagent of claim 11 wherein said reagent is in the form of a solution tablet, lyophilisate or, powder mixture or said reagent is applied to an appropriate carrier material.

14. The reagent of claim 11 wherein said derivative is selected from the group consisting of N-acetyldihydroresorufin-4-carboxylic acid morpholide, N-acetyl-8-bromodihydroresorufin-4-carboxylic acid morpholide, N-acetyldihydroresorufin-4-caboxylic acid carboxymethylamide and N-acetyl-8-chlorodihydroresorufin-4-carboxylic acid carboxymethylamide.

15. In a reagent for the determination of peroxidase, of compounds with peroxidase activity or of enzyme activities in systems producing hydrogen peroxide or peroxidate-acting compounds, wherein said reagent contains hydrogen peroxidase or peroxidate-acting substances, one or more chromogenic or fluorogenic substrates, necessary substrates and adjuvant enzymes, an appropriate buffer, further reagents and adjuvants, the improvement wherein an N-acyldihydroresorufin derivative according to claim 1 is used as a chromogenic or fluorogenic substrate.

16. The reagent of claim 15 wherein said derivative is selected from the group consisting of N-acetyldihydroresorufin-4-carboxylic acid morpholide, N-acetyl-8-bromodihydroresorufin-4-carboxylic acid morpholide, N-acetyldihydroresorufin-4-carboxylic acid carboxymethylamide and N-acetyl-8-chlorodihydroresorufin-4-carboxylic acid carboxy methylamide.

* * * * *

UNITED STATES PATENT AND TRADEMARK OFFICE
CERTIFICATE OF CORRECTION

PATENT NO. : 4,737,466                                      Page 1 of 2

DATED     : April 12, 1988

INVENTOR(S) : KLEIN et al.

It is certified that error appears in the above-identified patent and that said Letters Patent is hereby corrected as shown below:

Title page:

Abstract, line 1:    change "N-acylidihydroresorufin" to
                     -- N-acyldihydroresorufin --.

Abstract, add        -- The present invention also provides a
                     process for the preparation of these
                     derivatives and reagents containing them.
                     Furthermore, the present invention is
                     concerned with the use of these derivatives
                     for determining hydrogen peroxide,
                     peroxidate-acting compounds and
                     peroxidase. --.

UNITED STATES PATENT AND TRADEMARK OFFICE
CERTIFICATE OF CORRECTION

PATENT NO.   : 4,737,466
DATED        : April 12, 1988
INVENTOR(S)  : KLEIN et al.

It is certified that error appears in the above-identified patent and that said Letters Patent is hereby corrected as shown below:

Col. 9, line 1:      delete "N-acyl-dihydrosorufin" and insert -- N-acyl-dihydroresorufin --.

Col. 11, line 6:     after "(d, J=2.4 Hz, 1" insert -- H --.

Col. 11, line 64:    after "via", delete "6.8" and insert -- 6,8 --.

Col. 12, line 9:     after "(A)" delete "N,O,O-Turacetyldihyroresorufin" and insert -- N,O,O-Triacetyl-dihydroresorufin --.

Col. 12, line 67:    after (t, broad, J=) delete "7" and insert -- 6 --.

Col. 13, line 17:    after "-methylamide (" delete "RF" and insert -- Rf --.

Col. 16, line 33:    after "acids" insert -- of --.

Signed and Sealed this

Fourth Day of April, 1989

Attest:

DONALD J. QUIGG

Attesting Officer

Commissioner of Patents and Trademarks